United States Patent [19]

Fisher

[11] Patent Number: 4,502,506
[45] Date of Patent: Mar. 5, 1985

[54] VALVE

[75] Inventor: Kenneth J. Fisher, Erie, Pa.

[73] Assignee: American Sterilizer Company, Erie, Pa.

[21] Appl. No.: 452,123

[22] Filed: Dec. 22, 1982

[51] Int. Cl.³ ............................................. F16K 31/44
[52] U.S. Cl. .......................... 137/624.12; 137/624.18; 251/230
[58] Field of Search ...................... 137/624.11, 624.12, 137/624.18, 624.13, 624.2; 251/230

[56] References Cited

U.S. PATENT DOCUMENTS 3,474,620 7/1973 Kah .................................. 251/230 X
3,489,175 1/1970 Loveless .......................... 251/230 X Primary Examiner—Alan Cohan
Attorney, Agent, or Firm—Robert D. Yeager; Andrew Cornelius

[57] ABSTRACT

A valve permits articles disposed within a sterilizer container to be exposed to an entire sterilization cycle, yet seals the sterilizer container upon completion of the cycle. The valve includes a housing which defines a passage through which fluid can flow between the interior and exterior of the sterilizer container. A sealing member seals the passage after a predetermined number of high and low pressure stages of a sterilization cycle has been completed. A cam member is reciprocated as the high and low pressure stages of the sterilization cycle are performed, each reciprocation causing the sealing member to move one step closer toward sealing the sterilizer container. Apparatus is provided to permit the valve to be reset for further use of the container.

1 Claim, 5 Drawing Figures

VALVE

BACKGROUND OF THE INVENTION

1. Field of the Invention

The present invention relates to valves and, in particular, to a valve which opens or closes after a fluid proximate the valve has undergone a predetermined number of pressure cycles.

2. Description of the Prior Art

Often, medical equipment and instruments are sterilized within a chamber, referred to as a sterilizer, which contains a fluid that undergoes periodic variations in pressure as the articles are sterilized. Also, it is common for sterilized articles to be stored for a period of time after they are sterilized and before they are used. Of course, the sterilized articles must remain sterile during that time period.

Accordingly, workers in the art have developed a container for holding articles as they are sterilized. The container permits exposure of the articles to the fluid within the sterilizer during a part of the time the container is within the sterilizer. The container is sealed automatically upon completion of the sterilization cycle. Known containers generally employ a valve which is open when the pressure exerted by the fluid within the sterilizer is above a predetermined high value and is closed when the pressure is below a predetermined low value. Commonly, the sterilizer is under a high pressure condition when a sterilizing medium is present within the sterilizer. Therefore, the valve is open whenever the sterilizing medium is within the sterilizer to permit exposure of the articles within the container to the sterilizing medium, and is closed at all other times. When the sterilization cycle is completed, the pressure within the sterilizer is at the predetermined low value and the valve closes to seal the container and preserve the sterility of the articles after the container is removed from the sterilizer.

However, maximum sterilization and drying of the articles can be achieved only if the container is exposed to the interior of the sterilizer during the entire course of the sterilization cycle. With the use of the containers of the type described above, the articles within the container are exposed to the interior of the sterilizer only during a part of the sterilization cycle.

Therefore, there exists a need for a valve for a sterilizer container that permits exposure of the articles within the container to the entire sterilization cycle and seals the articles within the container upon completion of the sterilization cycle.

SUMMARY OF THE INVENTION

The present invention provides a valve for sealing an opening in a container after a predetermined number of pressure cycles have occurred outside the container. The valve includes a housing adapted to be so mounted to the container as to define a passage through which fluid can flow between the exterior and interior of the container. The valve also includes a sealing member so mounted to the housing as to be movable relative to the housing, the sealing member being capable of assuming a sealing position in which the sealing member blocks fluid flow through the passage, and at least one opened position in which the sealing member does not block fluid flow through the passage. The valve further includes a cam member so mounted to the housing as to be exposed to the pressure exerted by the fluid outside the container and to be movable relative to the sealing member. The cam member assumes a first position when the pressure exerted by the fluid outside the container is at the highest value within the range defined by the pressure cycle and a second position when the pressure exerted by the fluid outside the container is at the lowest value within the range. Movement of the cam member between the first and second positions, which is caused by the pressure exerted by the fluid outside the container varying between the highest and lowest values, causes the sealing member to assume an opened position if the predetermined number of pressure cycles has not occurred and to assume the sealing position if the predetermined number of pressure cycles has occurred. Finally, the valve includes apparatus for permitting the sealing member to be moved manually to an opened position.

The valve can include apparatus for biasing the sealing member toward the sealing position and a link that engages the cam member. The link is capable of assuming a freed position in which the biasing apparatus can move the sealing member toward the sealing position and a locked position in which the biasing apparatus cannot move the sealing member toward the sealing position. Movement of the cam member between the first and second positions causes the link to move between the freed and locked positions.

Accordingly, the present invention provides a valve that permits exposure of the interior of a sterilizer container to the entire sterilization cycle, yet seals the interior of the container upon completion of the cycle.

BRIEF DESCRIPTION OF THE DRAWINGS

The following detailed description of the preferred embodiments can be understood better if reference is made to the attached drawings in which.

DETAILED DESCRIPTION OF THE PREFERRED EMBODIMENTS

Figure 1:
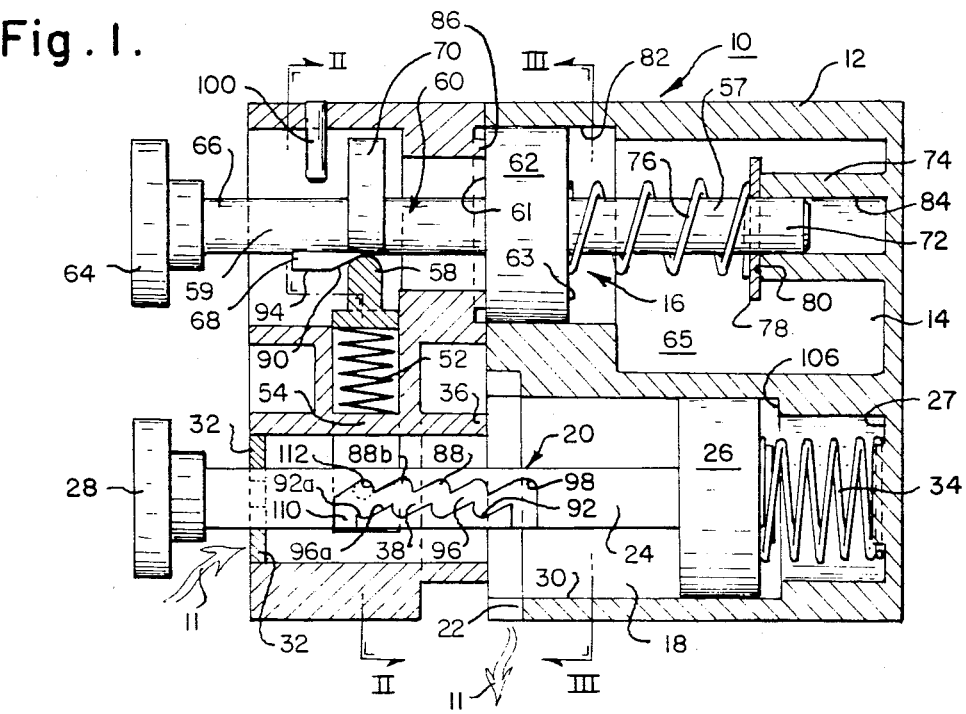
FIG. 1 is a sectional view of a valve constructed in accordance with the teachings of the present invention.
Figure 2:
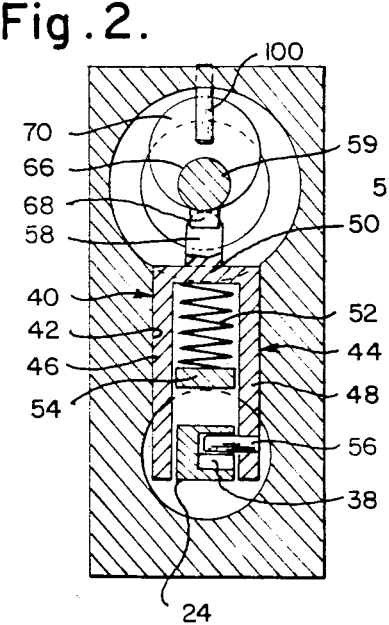
FIG. 2 is a sectional view of the valve shown in FIG. 1 taken along the line II—II.
Figure 3:
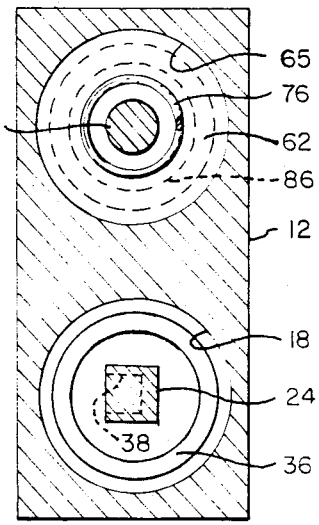
FIG. 3 is a sectional view of the valve shown in FIG. 1 taken along the line III—III.
Figure 4:
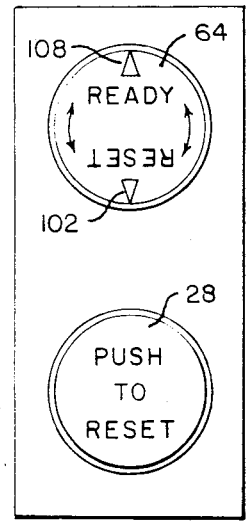
FIG. 4 is a front elevational view of the valve shown in FIG. 1.

FIG. 1 shows valve 10, which is the preferred embodiment of the present invention. Valve 10 is secured to a sterilizer container which contains articles to be sterilized. Generally, valve 10 includes a housing 12 that defines a chamber 14, which contains cam member 16, and a chamber 18, which contains sealing member 20. Housing 12 also defines a passage 22 which is in fluid communication with chamber 18 and the container to which valve 10 is mounted to provide a fluid path from within the sterilizer container to the exterior of valve 10 through chamber 18. Fluid flow into the container is indicated in FIG. 1 by arrows 11.

Sealing member 20 includes a rod 24, one end of which is secured to a piston 26 and the other end of which is secured to a button 28. Piston 26 is mounted for sliding movement within chamber 18 along cylindrical surface 30. Four slotted guides 32 guide the movement of rod 24 as piston 26 is moved along surface 30. Passage 22 is blocked, and, accordingly, the sterilizer container is sealed, when piston 26 is seated against valve seat 36. Compression spring 34 biases piston 26 toward valve seat 36. Preferably, the portion of chamber 18 between piston 26 and end 27 of chamber 18 is maintained under positive pressure to minimize the passage of fluid between the interior and exterior of the container while the container is being stored. Rod 24 defines a tortuous path 38, which will be described in more detail below.

Sealing member 20 also includes a link member 40 disposed for sliding movement within passage 42 defined by housing 12. Link 40 includes a yoke 44 made of two legs 46 and 48 and a top 50. A spring 52 is contained within passage 42 by yoke legs 46 and 48, yoke top 50 and a platform 54 which forms a part of the boundary of chamber 18. A pin 56 is secured to the bottom of leg 48 and is adapted to extend into tortuous path 38. A counterlink 58 is secured to yoke top 50 and extends into chamber 14.

Cam member 16 includes a shaft 60 upon which a piston 62 is mounted intermediate its ends and includes a button 64 secured to end 66 of shaft 60. Surface 61 of piston 62 should have a larger area than surface 63 to prevent the force exerted on surface 63 by fluid within chamber 65 from becoming equal to the force exerted on surface 61 as piston 62 compresses spring 76. In the preferred embodiment, portion 57 of shaft 60 has a larger diameter than portion 59 to cause surface 63 to have a lesser area than surface 61. A pair of cams 68 and 70 are formed on portion 59 of shaft 60. End 72 of portion 57 of shaft 60 is disposed within a mounting 74 which is secured to one end of housing 12 within chamber 65. Spring 76 is disposed around portion 57 of shaft 60 between surface 63 of piston 62 and mounting 74. Spring 76 is constrained by piston 62 and a washer 78 which is secured to surface 80 of mounting 74. The characteristics of spring 76 and the pressure exerted by fluid within chamber 65 determine the pressure retained within the sterilizer container at the end of the sterilization cycle.

Cam member 16 is mounted for sliding movement within chamber 14. Piston 62 and end 72 of shaft 60 slide along surface 82 of chamber 14 and surface 84 of mounting 74, respectively. Piston 62 seals chamber 65 regardless of its position on surface 82 and, further, maintains the seal as it travels along surface 82. The travel afforded piston 62 along surface 82 should not permit excessive pressure to be created in chamber 65. When piston 62 is in the position shown in FIG. 1, in which it is in contact with valve seat 86 of housing 12, cam 68 does not engage counterlink 58 and pin 56 is disposed against an upper seat 88 of tortuous path 38. As piston 62 is moved away from valve seat 86, cam ramp 90 forces counterlink 58 and link 40 down passage 42 and pin 56 becomes seated against a lower seat 92 of tortuous path 38, at which point counterlink 58 is resting on surface 94 of cam 68. When piston 62 subsequently moves back toward valve seat 86 counterlink 58 rides down a cam ramp 90, link 40 moves toward cam member 16 and spring 34 urges both piston 26 and shaft 24 toward valve seat 36 as pin 56 rides up a ramp portion 96 of tortuous path 38.

Figure 5:
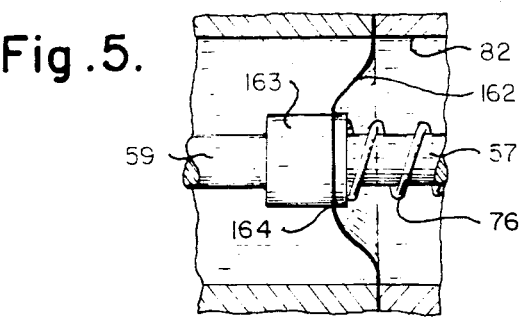
FIG. 5 is a diagrammatic view showing a diaphragm that is part of an alternate embodiment of the present invention.

FIG. 5 shows part of the cam member of an alternate embodiment of the present invention. The alternate embodiment is identical to valve 10 with the exception that an appropriate diaphragm 162, or a bellows, replaces piston 62. Diaphragm 162 is deflected toward or away from chamber 65 as the pressure outside the valve varies, thus operating sealing member 20 in the manner described above. As is shown in FIG. 5, the edge of diaphragm 162 is secured to surface 82. Diaphragm 162 defines an opening 164 which receives a hub 163. Hub 163 is secured to diaphragm 162 at the border of opening 164. Accordingly, movement of the central portion of diaphragm 162 toward and away from chamber 65 causes shaft 60 to reciprocate and operate sealing member 20.

At the end of a sterilization cycle, pin 56 is disposed in the end upper seat 98 of tortuous path 38 and piston 26 is seated against valve seat 36, thus sealing the sterilizer container to which the valve 10 is mounted. To prepare the sterilizer container for use in another sterilization cycle, button 64 is rotated until arrow 102 points directly away from button 28, and cam 68 engages a stop pin 100 secured to the inside of housing 12 within chamber 14. As button 64 is so rotated, cam 70 engages counterlink 58 and causes pin 56 to travel down end passage 104 and out of engagement with shaft 24. Then, button 28 can be pushed toward the interior of valve 10 until piston 26 is seated against shoulder 106 of housing 12. Button 64 is then rotated until arrow 108 points directly away from button 28. As button 64 is so rotated, cam 70 becomes disengaged from counterlink 58 and pin 56 travels up end passage 110. Spring 34 moves piston 26 toward valve seat 36 until pin 56 becomes seated in end upper seat 112, at which point the sterilizer container is ready to be placed in the sterilizer. Then, the sterilization cycle is commenced. During the first high pressure stage of the cycle, pressure is exerted against piston 62 which causes it to move away from valve seat 86 and compress spring 76. Counterlink 58 rides up cam ramp 90 and becomes seated on surface 94 which causes pin 56 to become seated on lower seat 92a. During the next low pressure stage of the sterilization cycle, spring 76 urges piston 62 into engagement with valve seat 86 and counterlink 58 travels down ramp 90, thereby causing pin 56 to travel along ramp 96a to upper seat 88b, which permits compressed spring 34 to urge piston 26 further toward valve seat 36. Accordingly, successive high and low pressure stages of the sterilization cycle cause piston 26 to move toward valve seat 36 as pin 56 moves along tortuous path 38 until it is seated in upper seat 98 and piston 26 blocks passage 22 to seal the sterilizer container, at which point the sterilization cycle has been completed. The sterilizer container can be removed from the sterilizer and placed in storage with the assurance that the articles within the sterilizer container will remain sterile until the container is opened.

What is claimed is:

1. A valve for sealing an opening in a container after a predetermined number of pressure cycles have occurred outside the container comprising:

a housing adapted to be so mounted to the container as to define a passage through which fluid can flow between the exterior and interior of the container;

a sealing member so mounted to said housing as to be movable relative to said housing, said sealing member being capable of assuming a sealing position in which said sealing member blocks fluid flow through said passage, and at least one opened position in which said sealing member does not block fluid flow through said passage;

a cam member so mounted to said housing as to be exposed to the pressure exerted by the fluid outside the container and to be movable relative to said sealing member, said cam member assuming a first position when the pressure exerted by the fluid outside the container is at the highest value within the range define by the pressure cycle and a second position when the pressure exerted by the fluid outside the container is at the lowest value within the range, movement of said cam member between said first and second positions, caused by the pressure exerted by the fluid outside the container varying between said highest and lowest values, causing said sealing member to assume said opened position if said predetermined number of pressure cycles has not occurred and to assume said sealing position if said predetermined number of pressure cycles has occurred; and means for permitting said sealing member to be moved manually to an opened position;

said sealing member including means for biasing said sealing member toward said sealing position and a link that engages said cam member, said link being capable of assuming a freed position in which said biasing means can move said sealing member toward said sealing position and a locked position in which said biasing means cannot move said sealing member toward said sealing position, movement of said cam member between said first and second positions causing said link to move between said freed and locked positions.

* * * * *